US011215601B2

(12) United States Patent
Pomedli

(10) Patent No.: US 11,215,601 B2
(45) Date of Patent: Jan. 4, 2022

(54) SYSTEM FOR MONITORING SOIL CONDITIONS BASED ON ACOUSTIC DATA AND ASSOCIATED METHODS FOR ADJUSTING OPERATING PARAMETERS OF A SEED-PLANTING IMPLEMENT BASED ON MONITORED SOIL CONDITIONS

(71) Applicant: CNH Industrial Canada, Ltd., Saskatoon (CA)

(72) Inventor: Barry M. Pomedli, Saskatoon (CA)

(73) Assignee: CNH Industrial Canada, Ltd., Saskatoon (CA)

( * ) Notice: Subject to any disclaimer, the term of this patent is extended or adjusted under 35 U.S.C. 154(b) by 559 days.

(21) Appl. No.: 16/170,303

(22) Filed: Oct. 25, 2018

(65) Prior Publication Data
US 2020/0132654 A1     Apr. 30, 2020

(51) Int. Cl.
| | |
|---|---|
| A01B 79/00 | (2006.01) |
| G01N 33/24 | (2006.01) |
| A01C 5/06 | (2006.01) |
| A01C 7/10 | (2006.01) |
| A01B 63/32 | (2006.01) |
| A01C 21/00 | (2006.01) |
| G06F 16/29 | (2019.01) |

(52) U.S. Cl.
CPC ............ *G01N 33/24* (2013.01); *A01B 63/32* (2013.01); *A01B 79/005* (2013.01); *A01C 5/064* (2013.01); *A01C 7/102* (2013.01); *A01C 21/00* (2013.01); *G06F 16/29* (2019.01); *G01N 2033/245* (2013.01)

(58) Field of Classification Search
CPC ....... A01B 63/32; A01B 79/005; A01C 5/064; A01C 7/102; A01C 21/00; G01N 33/24; G01N 2033/245; G06F 16/29
See application file for complete search history.

(56) References Cited

U.S. PATENT DOCUMENTS

| | | | | |
|---|---|---|---|---|
| 3,744,586 | A | * | 7/1973 | Leinauer ............... G01S 13/931 180/401 |
| 4,905,897 | A | | 3/1990 | Rogers et al. |
| 5,831,542 | A | | 11/1998 | Thomas et al. |
| 6,296,425 | B1 | | 10/2001 | Memory et al. |
| 8,074,586 | B2 | | 12/2011 | Garner et al. |

(Continued)

FOREIGN PATENT DOCUMENTS

WO     WO2016/032457 A1     3/2016

OTHER PUBLICATIONS

AGCO Technologies, Wireless Blockage and Flow Monitor, FUSE, 2018, 3 pages. https://www.agcotechnologies.com/products/detail/wireless-blockage-flow-monitor/.

*Primary Examiner* — Jamie L McGowan
(74) *Attorney, Agent, or Firm* — Rebecca L. Henkel; Rickard K. DeMille

(57) ABSTRACT

In one aspect, a system for monitoring soil conditions within an agricultural field may include a furrow forming tool. The system may also include an acoustic sensor configured to detect a sound associated with movement of the furrow forming tool through the soil. Furthermore, the system may include a controller communicatively coupled to the acoustic sensor. The controller may be configured to monitor a soil condition associated with soil within the field based on acoustic data received from the acoustic sensor.

20 Claims, 5 Drawing Sheets

(56) References Cited

U.S. PATENT DOCUMENTS

| | | |
|---|---|---|
| 8,448,587 B2 * | 5/2013 | Kowalchuk ............ A01C 7/105 |
| | | 111/200 |
| 8,504,310 B2 | 8/2013 | Landphair et al. |
| 8,618,465 B2 | 12/2013 | Tevs et al. |
| 8,695,396 B2 | 4/2014 | Landphair et al. |
| 8,950,260 B2 | 2/2015 | Gelinske et al. |
| 9,565,798 B2 | 2/2017 | Baker |
| 9,580,256 B2 | 2/2017 | Wagers et al. |
| 9,631,964 B2 | 4/2017 | Geliaske et al. |
| 9,883,626 B2 * | 2/2018 | Heim ..................... A01C 7/102 |
| 2015/0305226 A1 * | 10/2015 | Zemenchik ............ A01C 7/102 |
| | | 701/50 |
| 2015/0355003 A1 | 12/2015 | Saeger et al. |
| 2016/0246296 A1 | 8/2016 | Gelinske et al. |
| 2017/0102259 A1 | 4/2017 | do Amaral Assy et al. |
| 2018/0168094 A1 * | 6/2018 | Koch ..................... A01C 7/203 |
| 2019/0124824 A1 * | 5/2019 | Hubner ................. A01C 5/064 |
| 2019/0289786 A1 * | 9/2019 | Prystupa .............. G01N 33/025 |

* cited by examiner

SYSTEM FOR MONITORING SOIL CONDITIONS BASED ON ACOUSTIC DATA AND ASSOCIATED METHODS FOR ADJUSTING OPERATING PARAMETERS OF A SEED-PLANTING IMPLEMENT BASED ON MONITORED SOIL CONDITIONS

FIELD OF THE INVENTION

The present disclosure generally relates to seed-planting implements and, more particularly, to systems for monitoring soil conditions encountered by a seed-planting implement based on acoustic data and associated methods for adjusting operating parameters of the seed-planting implement based on the monitored soil conditions.

BACKGROUND OF THE INVENTION

Modern farming practices strive to increase yields of agricultural fields. In this respect, seed-planting implements are towed behind a tractor or other work vehicle to disperse seed throughout a field. For example, seed-planting implements typically include one or more furrow forming tools or openers that form a furrow or trench in the soil. One or more dispensing devices of the seed-planting implements may, in turn, deposit the seeds into the furrow(s). After deposition of the seeds, a packer wheel may pack the soil on top of the deposited seeds.

A seed-planting implement may encounter differing soil conditions as it is moved across a field. For example, the soil roughness or "bumpiness" may vary from one portion of the field to another. Moreover, impediments (e.g., rocks) may be present within the soil at various locations within the field. As such, when the soil conditions change, it may be necessary to adjust one or more operating parameters of the seed-planting implement. For example, when soil roughness increases, it may be necessary to increase the down pressure applied to the furrow forming tool(s) to maintain a uniform furrow depth. However, it may be difficult for the operator of the seed-planting implement to identify when soil conditions change.

Accordingly, an improved system for monitoring soil conditions and associated method for adjusting operating parameters of a seed-planting implement based on monitored soil conditions would be welcomed in the technology.

SUMMARY OF THE INVENTION

Aspects and advantages of the technology will be set forth in part in the following description, or may be obvious from the description, or may be learned through practice of the technology.

In one aspect, the present subject matter is directed to a system for monitoring soil conditions within an agricultural field. The system may include a furrow forming tool and an acoustic sensor configured to detect a sound associated with movement of the furrow forming tool through the soil. The system may also include a controller communicatively coupled to the acoustic sensor. The controller may be configured to monitor a soil condition associated with soil within the field based on acoustic data received from the acoustic sensor.

In another aspect, the present subject matter is directed to a seed-planting implement having a frame and a furrow forming tool mounted on the frame and configured to form a furrow within the soil. The seed-planting implement may also include an acoustic sensor configured to detect a sound associated with movement of the furrow forming tool through the soil. The seed-planting implement may further include an acceleration sensor configured to detect a parameter associated with movement of the furrow forming tool relative to the frame. Furthermore, seed-planting implement may include a controller communicatively coupled to the acoustic sensor and the acceleration sensor. As such, the controller may be configured to monitor a soil condition associated with soil within the field based on data received from the acoustic sensor and the acceleration sensor.

In a further aspect, the present subject matter is directed to a method for controlling operating parameters of a seed-planting implement based on monitored soil conditions of an agricultural field. The seed-planting implement may include a furrow forming tool. The method may include receiving, with a computing device, acoustic data indicative of a sound associated with movement of the furrow forming tool through soil within a field. The method may also include determining, with the computing device, a soil condition of the soil within the field based on the received acoustic data. Furthermore, the method may include initiating, with the computing device, a control action associated with adjusting an operating parameter of the seed-planting implement based on the determined soil condition.

These and other features, aspects and advantages of the present technology will become better understood with reference to the following description and appended claims. The accompanying drawings, which are incorporated in and constitute a part of this specification, illustrate embodiments of the technology and, together with the description, serve to explain the principles of the technology.

BRIEF DESCRIPTION OF THE DRAWINGS

A full and enabling disclosure of the present technology, including the best mode thereof, directed to one of ordinary skill in the art, is set forth in the specification, which makes reference to the appended figures, in which.

Figure 1:
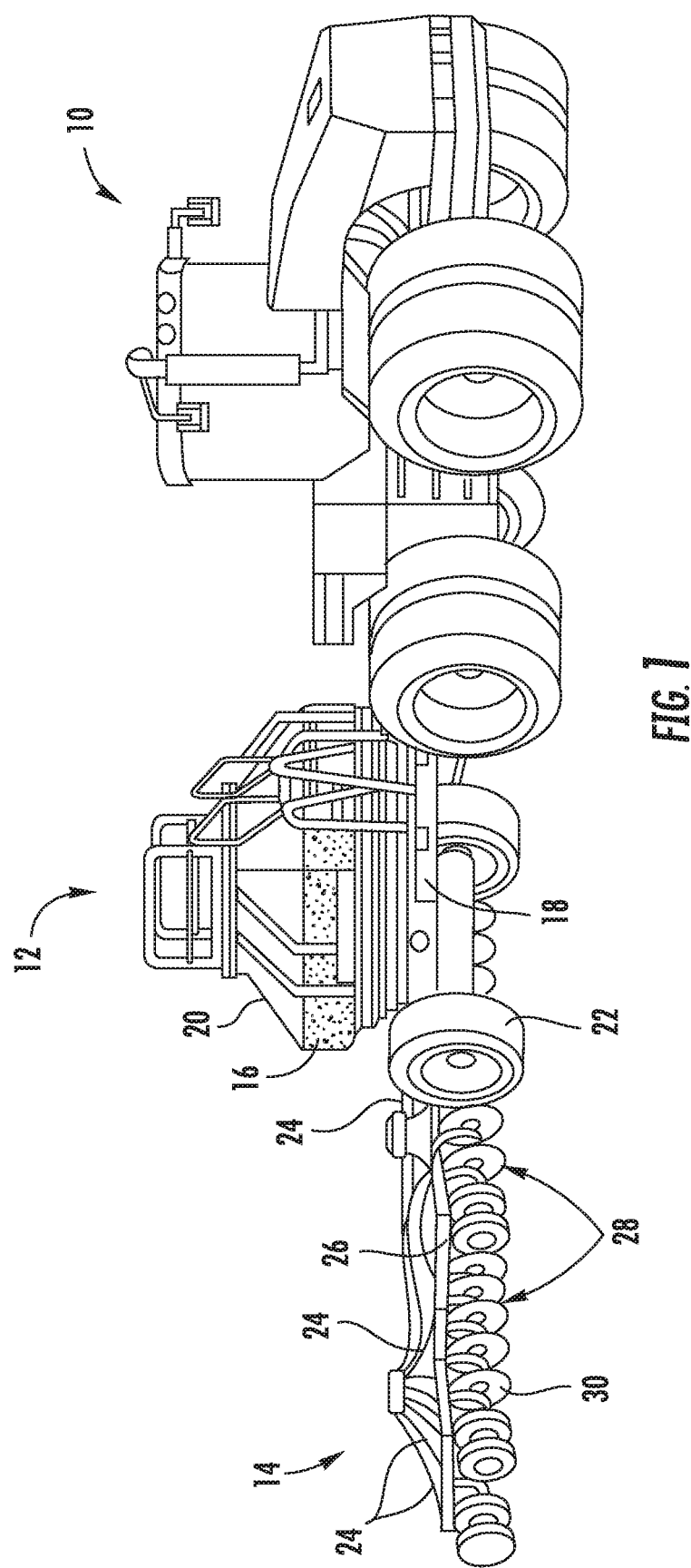
FIG. 1 illustrates a perspective view of one embodiment of a work vehicle, an air cart, and a seed-planting implement in accordance with aspects of the present subject matter.

Repeat use of reference characters in the present specification and drawings is intended to represent the same or analogous features or elements of the present technology.

DETAILED DESCRIPTION OF THE DRAWINGS

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

In general, the present subject matter is directed to systems for monitoring soil conditions and associated methods for adjusting operating parameters of an implement based on monitored soil conditions. Specifically, in several embodiments, a controller of the disclosed system may be configured to receive acoustic data as the implement is moved across the field. For example, in one embodiment, the acoustic data may be indicative of a sound(s) associated with movement of one or more furrow forming tools of the implement, such as a disc opener(s) or a hoe opener(s), through the soil. As such, the controller configured to analyze the received acoustic data to monitor one or more soil conditions associated with the soil within the field, such as the soil roughness of and/or the presence of soil impediments (e.g., rocks) with the soil. Thereafter, the controller may further be configured to initiate a control action associated with adjusting an operating parameter of the seed-planting implement based on the monitored soil condition(s). For instance, the controller may be configured to adjust the down pressure applied to the furrow forming tool(s).

Referring now to drawings, FIG. 1 illustrates a perspective view of one embodiment of a work vehicle 10, an air cart 12, and a seed-planting implement or planter 14 in accordance with aspects of the present subject matter. It should be appreciated that, although the work vehicle 10 illustrated herein is configured as a tractor, the work vehicle 10 may generally be configured as any suitable work vehicle known in the art, such as any other agricultural vehicle. It should also be appreciated that, although the seed-planting implement 14 illustrated herein corresponds to a seed disc drill, the seed-planting implement 14 may generally correspond to any suitable equipment or implement, such as seed hoe drill or another seed dispensing implement (e.g., a planter), a side dresser or another fertilizer dispensing implement, a strip tiller, and/or the like.

As shown, the air cart 12 may be configured to be towed directly behind the work vehicle 10, with the seed-planting implement 14 being towed behind the air cart 12. In this regard, a hitch assembly (not shown) may be configured to couple the air cart 12 to the work vehicle 10. Furthermore, another hitch assembly (not shown) may be configured to couple the seed-planting implement 14 to the air cart 12. However, in an alternative embodiment, the seed-planting implement 14 may be towed directly behind the work vehicle 10, with the air cart 12 being towed behind the seed-planting implement 14. In a further embodiment, the air cart 12 and the seed-planting implement 14 may be part of a single unit that is towed behind the work vehicle 10, or elements of a self-propelled vehicle configured to distribute agricultural product across a field.

In accordance with aspects of the present disclosure, the air cart 12 may be configured to store a flowable liquid or granular agricultural product 16, such as seeds, fertilizer, and/or the like, to be deposited within the soil. Specifically, in several embodiments, the air cart 12 may include a frame 18 configured to support or couple to various components of the air cart 12. For example, as shown, the frame 18 may be configured to support a hopper or storage tank 20 configured for storing the agricultural product 16 to be deposited within the furrow. Furthermore, in one embodiment, a plurality of wheels 22 may be coupled to the frame 18 to permit the air cart 12 to be towed across a field by the work vehicle 10. Additionally, a plurality of delivery conduits 24 may be configured to convey the agricultural product 16 from the air cart 12 to the seed-planting implement 14 for deposition into the furrow.

In several embodiments, the seed-planting implement 14 may include a toolbar 26 configured to support or couple to various components of the seed-planting implement 14, such as one or more row units 28. As will be described below, each row unit 28 may include one or more furrow forming tools, such as the illustrated disc openers 30, configured to excavate a furrow or trench in soil to facilitate deposition of the agricultural product 16. It should be appreciated that the seed-planting implement 14 may generally include any number of row units 28 to facilitate delivery of the agricultural product 16 across a given swath of the soil. For instance, in one embodiment, the seed-planting implement 14 may include twenty-four row units 28 spaced apart across the width of the seed-planting implement 14. In alternative embodiments, however, the seed-planting implement 14 may include any other suitable number of row units 28, such as less than twenty-four row units 28 or more than twenty-four row units 28. Moreover, it should be appreciated that, in alternative embodiments, the furrow forming tool(s) may be configured as a hoe(s), a coulter(s), or any other suitable tool(s).

Figure 2:
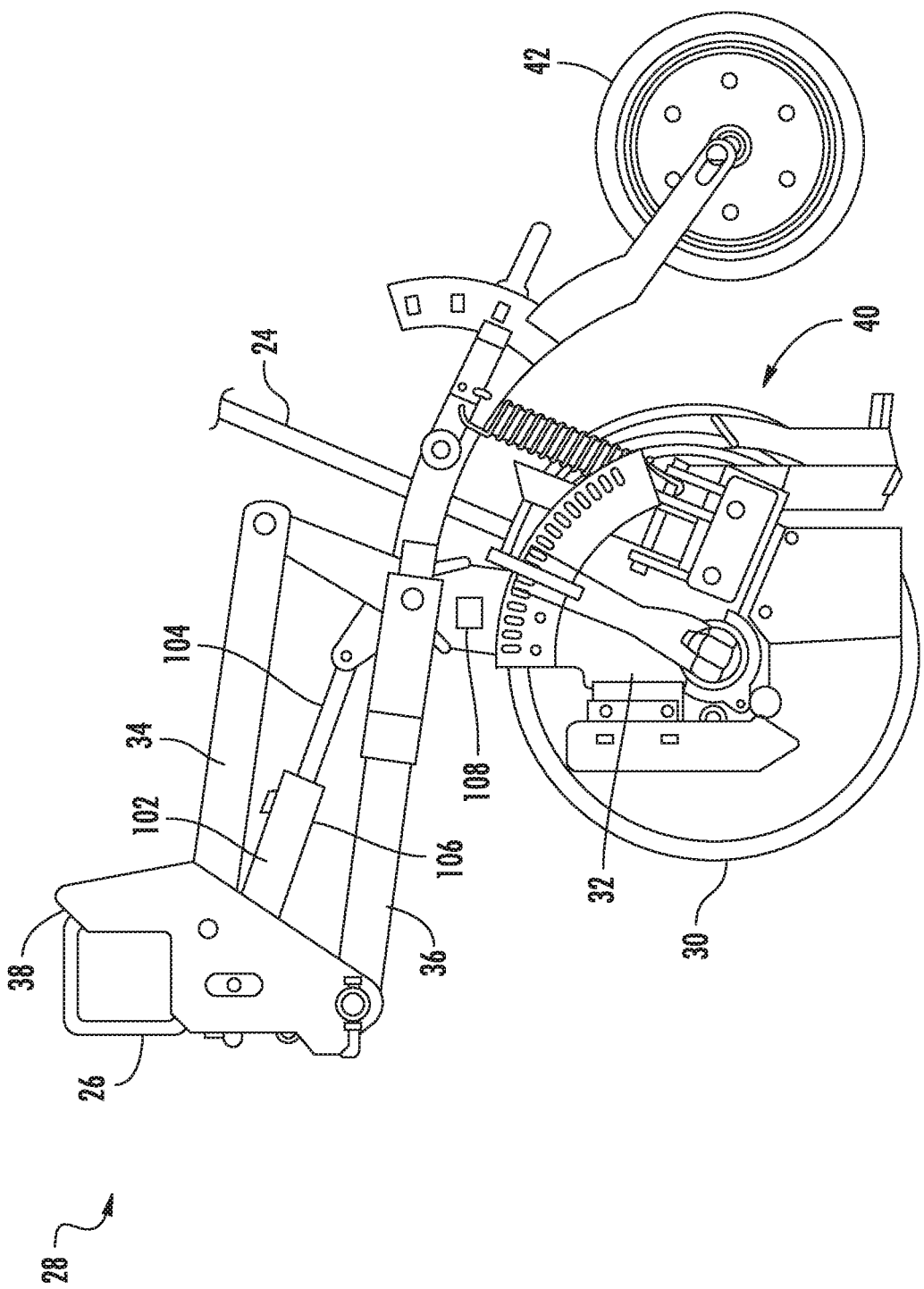
FIG. 2 illustrates an side view of one embodiment of a row unit of a seed-planting implement in accordance with aspects of the present subject matter.

Referring now to FIG. 2, a side view of one embodiment of a row unit 28 is illustrated in accordance with aspects of the present subject matter. As shown, the row unit 28 may include a frame member or backbone 32 adjustably coupled to the toolbar 26 by upper and lower links 34, 36. For example, one end of each upper and lower link 34, 36 may be pivotably coupled to the frame member 32, while an opposed end of each upper and lower link 34, 36 may be pivotably coupled to a bracket 38, which is, in turn, coupled to the toolbar 26. In one embodiment, the upper and lower links 34, 36 may be parallel. However, it should be appreciated that, in alternative embodiments, the row unit 28 may be coupled to the toolbar 26 in any other suitable manner. For example, the upper and/or lower links 34, 36 may be fixedly coupled to the frame member 32 and/or the links 34, 36 may be non-parallel. Additionally, in a further embodiment, the seed-planting implement 14 may not include the upper and/or lower links 34, 32. In such instance, the seed-planting implement 14 may include other components for coupling each row unit 28 to the toolbar 26.

As shown in FIG. 2, the row unit 28 may also include a furrow opening assembly 40, a furrow closing assembly (not shown), and a press wheel 50. In general, the furrow opening assembly 40 may include one or more furrow forming tools, such as the disc opener(s) 30, which are configured to excavate a furrow or trench in the soil for the deposition of the agricultural product 16. The furrow closing assemblies are not shown to better illustrate the disc openers 30. As is generally understood, each furrow closing assembly may include a closing disc(s) configured to close the furrow after seeds have been deposited into the furrow. The press wheel 42 may then be configured to roll over the corresponding closed furrow to firm the soil over the seeds and promote favorable seed-to-soil contact.

Additionally, in several embodiments, an actuator 102 may be configured to move or otherwise adjust the position of the row unit 28 relative to the toolbar 26. For example, as shown in the illustrated embodiment, a first end of the actuator 102 (e.g., a rod 104 of the actuator 102) may be coupled to the frame member 32 of the row unit 28, while a second end of the actuator 102 (e.g., the cylinder 106 of the actuator 102) may be coupled to the bracket 38, which is, in turn, coupled to the toolbar 26. The rod 104 of the actuator 102 may be configured to extend and/or retract relative to the cylinder 106 to adjust the down pressure being applied to the disc opener(s) 30. In addition, such extension and/or retraction may move the row unit 28 between an operating position relative to the ground in which the disc opener(s) 30 engages the soil and a raised position relative to the ground in which the disc opener(s) is lifted out of the soil. In the illustrated embodiment, the actuator 102 corresponds to a fluid-driven actuator, such as hydraulic or pneumatic cylinder. However, it should be appreciated that the actuator 102 may correspond to any other suitable type of actuator, such as an electric linear actuator.

Moreover, an acceleration sensor 108 may be provided in operative association with the row unit 28. In several embodiments, the acceleration sensor 108 may be configured to detect a parameter associated with movement of the row unit 28 and, more specifically, the disc opener(s) 30 relative to the toolbar 26. As such, in one embodiment, the acceleration sensor 108 may be mounted on or otherwise provided in operative association with the backbone 32 of the row unit 28. However, it should be appreciated that, in alternative embodiments, the acceleration sensor 108 may be installed on or provided in operative association with any other component of the row unit 28 that permits the acceleration sensor 108 to detect movement of the disc opener(s) 30 relative to the toolbar 26. For example, in one embodiment, the acceleration sensor 108 may be embedded within a cavity (not shown) defined by one of the disc openers 30. Furthermore, it should be appreciated that the acceleration sensor 108 may be configured as any suitable type of acceleration sensor, such as a piezoelectric acceleration sensor (e.g., three-axis piezoelectric accelerometer), a gyroscope, an inertial measurement unit, and/or the like.

Figure 3:
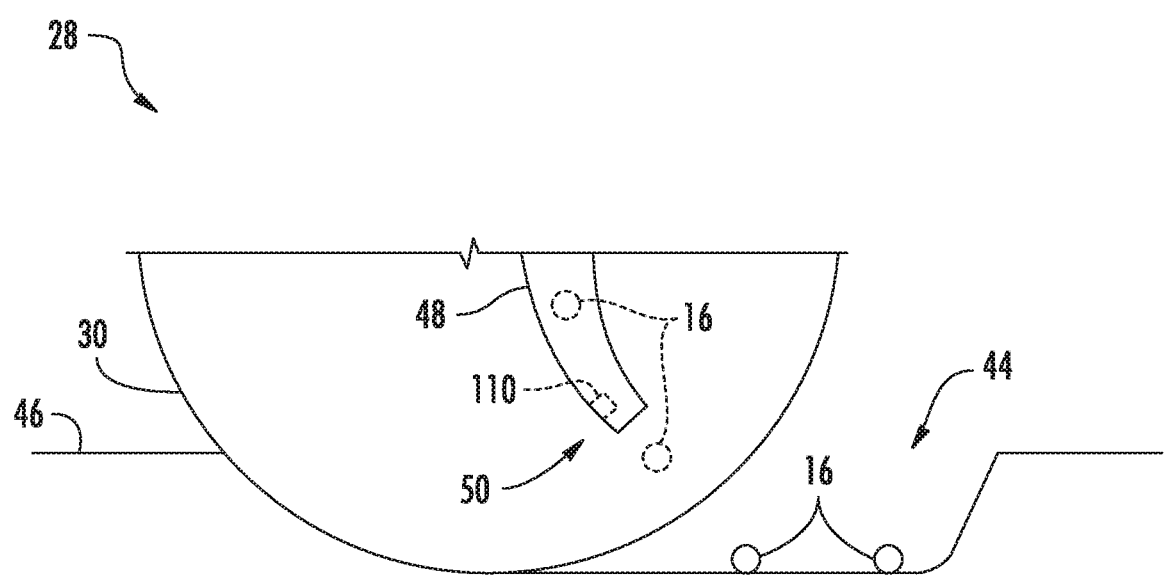
FIG. 3 illustrates an enlarged, partial side view of the row unit shown in FIG. 2, particularly illustrating an acoustic sensor of the row unit in accordance with aspects of the present subject matter.

Referring now to FIG. 3, an enlarged, partial side view of the row unit 28 is illustrated in accordance with aspects of the present subject matter. As indicated above, the disc opener(s) 30 of the row unit 28 may be configured to form a furrow 44 within the soil 46 for deposition of the agricultural product 16. In this regard, in several embodiments, the row unit 28 may also include a seed tube 48 configured to convey the agricultural product 16 to the furrow 44. For example, in one embodiment, a seed meter (not shown) may be configured to dispense the agricultural product 16 received from the hopper 20 of the air cart 12 (e.g., via the delivery conduits 24) into the seed tube 48 at a rate that corresponds to the desired spacing of the agricultural product 16 within the furrow 44. Thereafter, the agricultural product 16 may travel through the seed tube 48 (e.g., via gravity) for delivery to the furrow 44.

In accordance with aspects of the present subject matter, an acoustic sensor 110 may be provided in operative association with the row unit 28. Specifically, in several embodiments, the acoustic sensor 110 may be configured to detect a sound(s) associated with movement of the disc opener(s) 30 through the soil 46. As will be described below, such sound(s) may be indicative of one or more soil conditions of the soil 46. In this regard, the acoustic sensor 110 may be installed on the row unit 28 at any suitable position adjacent to the disc opener(s) 30. For example, in one embodiment, the acoustic sensor 110 may be installed within or otherwise provided in operative association with the seed tube 48, such as at or adjacent to a downstream end 50 of the seed tube 48. In another embodiment, the acoustic sensor 110 may be embedded within a cavity (not shown) defined by one of the disc openers 30. Furthermore, in one embodiment, the acoustic sensor 110 may be configured as a microphone. However, it should be appreciated that, in alternative embodiments, the acoustic sensor 110 may be provided in operative association with any other suitable component(s) of the row unit 28 and/or may be configured as any other suitable type of sensor.

In one embodiment, the acoustic sensor 110 may be configured to detect a sound(s) associated with delivery of the agricultural product 16 to the furrow 44. As indicated above, in one embodiment, the acoustic sensor 110 may be positioned within the seed tube 48. In such embodiment, the acoustic sensor 110 may be configured to detect the sound(s) of the agricultural product 16 contacting the sensor 110. As will be described below, such sound(s) may be indicative of when the agricultural product 16 is deposited into the furrow 44. However, it should be appreciated that, in alternative embodiments, the acoustic sensor 110 may be configured to detect the sound(s) associated with delivery of the agricultural product 16 to the furrow 44 in any other suitable manner. Furthermore, it should be appreciated that, in further embodiments, the acoustic sensor 110 may be configured to detect the sound(s) associated with movement of the disc opener(s) 30 through the soil 46 and a second acoustic sensor (not shown) detect the sound(s) associated with delivery of the agricultural product 16 to the furrow 44.

Although the acceleration sensor 108 and the acoustic sensor 110 are shown in FIGS. 2 and 3 as separate devices mounted in different locations on the row unit 28, the sensors 108, 110 may form part of a sensor assembly. For example, in one embodiment, the sensor assembly may include several sensors (e.g., the sensors 108, 110 and/or other sensors, such as a temperature sensor) assembled together or otherwise packaged into a single modular device that may be installed on the row unit 28 at a single location. As such, the sensor assembly may reduce the installation time of the sensors 108, 110 on the row unit 28 and/or facilitate retrofitting of existing row units with the sensors 108, 110.

Additionally, it should also be appreciated that the configuration of the seed-planting implement 14 described above and shown in FIGS. 1-3 is provided only to place the present subject matter in an exemplary field of use. Thus, it should be appreciated that the present subject matter may be readily adaptable to any manner of implement configuration. For example, in alternative embodiments, the implement may be configured as another type of seed-planting implement, such as a hoe disc drill, or another type of implement entirely, such as a tillage implement.

Figure 4:
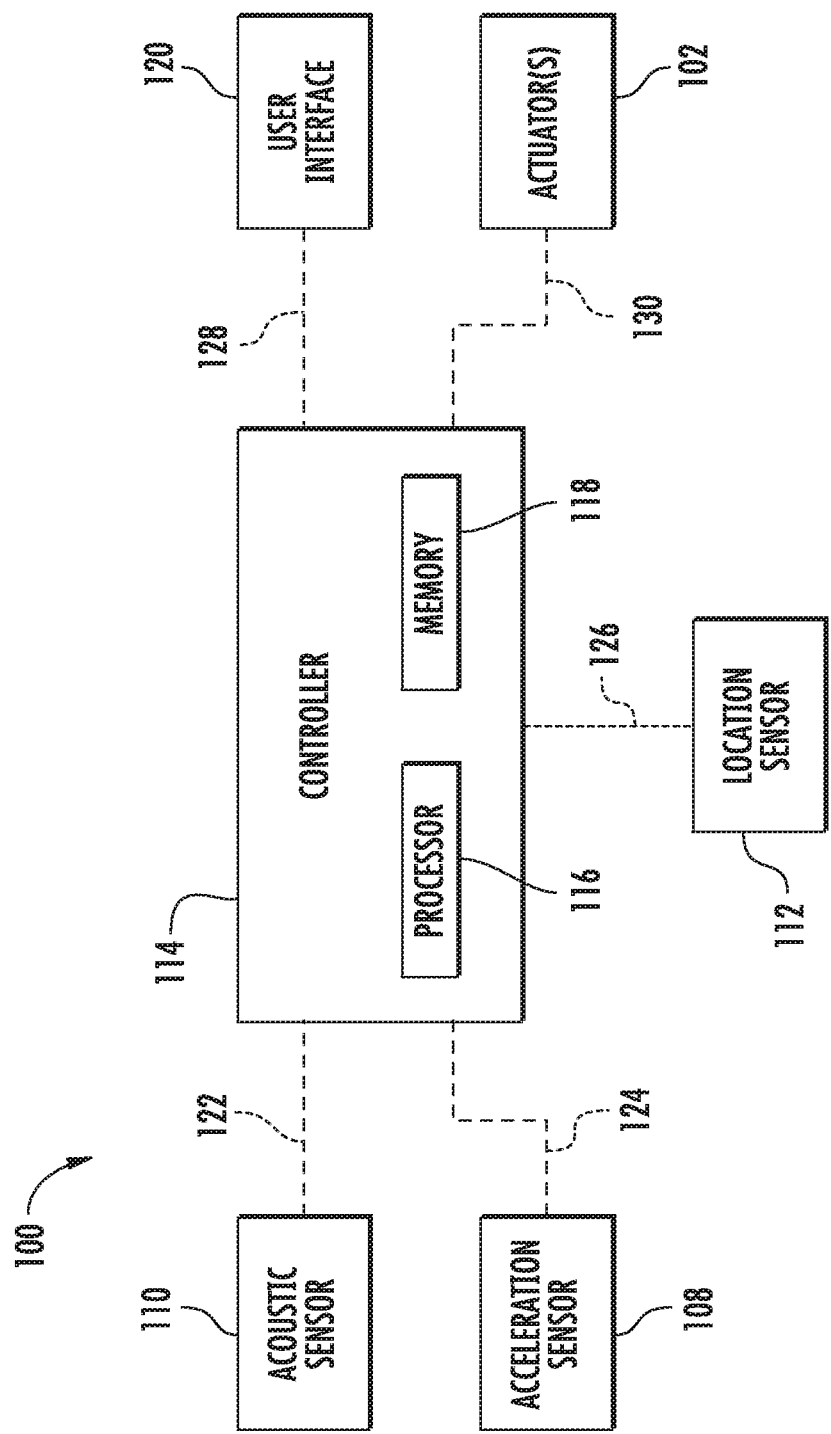
FIG. 4 illustrates a schematic view of one embodiment of a system for monitoring soil conditions in accordance with aspects of the present subject matter.

Referring now to FIG. 4, a schematic view of one embodiment of a system 100 for monitoring soil conditions is illustrated in accordance with aspects of the present subject matter. In general, the system 100 will be described herein with reference to the seed-planting implement 14 described above with reference to FIGS. 1-3. However, it should be appreciated by those of ordinary skill in the art that the disclosed system 100 may generally be utilized with seed-planting implements having any other suitable seed-planting implement configuration.

As shown, in several embodiments, the system 100 may include a location sensor 112 configured to detect a parameter associated with a geographical or physical location of the seed-planting implement 14 within the field. For instance, in one embodiment, the location sensor 112 may correspond to a GNSS-based receiver configured to detect the GNSS coordinates of the work vehicle 10, the air cart 12, and/or the seed-planting implement 14. As such, the location sensor 112 may mounted on the work vehicle 10, the air cart 12, and/or the seed-planting implement 14. However, it should be appreciated that, in alternative embodiments, the location sensor 112 may be configured as any suitable location sensing device for detecting the location of the work vehicle 10, the air cart 12, and/or the seed-planting implement 14.

In accordance with aspects of the present subject, the system 100 may include a controller 114 configured to electronically control the operation of one or more components of the seed-planting implement 14. In general, the controller 114 may comprise any suitable processor-based device known in the art, such as a computing device or any suitable combination of computing devices. Thus, in several embodiments, the controller 114 may include one or more processor(s) 116 and associated memory device(s) 118 configured to perform a variety of computer-implemented functions. As used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. Additionally, the memory device(s) 118 of the controller 114 may generally comprise memory element(s) including, but not limited to, a computer readable medium (e.g., random access memory (RAM)), a computer readable non-volatile medium (e.g., a flash memory), a floppy disk, a compact disc-read only memory (CD-ROM), a magneto-optical disk (MOD), a digital versatile disc (DVD) and/or other suitable memory elements. Such memory device(s) 118 may generally be configured to store suitable computer-readable instructions that, when implemented by the processor(s) 116, configure the controller 114 to perform various computer-implemented functions, such as one or more aspects of the method 200 described below with reference to FIG. 5. In addition, the controller 114 may also include various other suitable components, such as a communications circuit or module, one or more input/output channels, a data/control bus and/or the like.

It should be appreciated that the controller 114 may correspond to an existing controller of the work vehicle 10, the air cart 12, or the seed-planting implement 14 or the controller 114 may correspond to a separate processing device. For instance, in one embodiment, the controller 114 may form all or part of a separate plug-in module that may be installed within the work vehicle 10, the air cart 12, or the seed-planting implement 14 to allow for the disclosed system and method to be implemented without requiring additional software to be uploaded onto existing control devices of the work vehicle 10, the air cart 12, or the seed-planting implement 14.

Furthermore, in one embodiment, the system 100 may also include a user interface 120. More specifically, the user interface 120 may be configured to provide feedback (e.g., information associated with the monitored soil conditions) to the operator of the seed-planting implement 14. As such, the user interface 120 may include one or more feedback devices (not shown), such as display screens, speakers, warning lights, and/or the like, which are configured to communicate such feedback. In addition, some embodiments of the user interface 120 may include one or more input devices (not shown), such as touchscreens, keypads, touchpads, knobs, buttons, sliders, switches, mice, microphones, and/or the like, which are configured to receive user inputs from the operator. In one embodiment, the user interface 120 may be positioned within a cab (not shown) of the work vehicle 10. However, in alternative embodiments, the user interface 120 may have any suitable configuration and/or be positioned in any other suitable location.

In several embodiments, the controller 114 may be configured to receive acoustic data indicative of a sound(s) associated with movement of a furrow forming tool(s), such as the disc opener(s) 30, through soil as the seed-planting implement 14 is moved across the field. Specifically, as shown in FIG. 4, the controller 114 may be communicatively coupled to the acoustic sensor 110 via a wired or wireless connection to allow acoustic data (e.g., indicated by dashed line 122 in FIG. 4) to be transmitted from the acoustic sensor 110 to the controller 114. For example, in one embodiment, the controller 114 may be configured to continuously receive the acoustic data 122 as the seed-planting implement 14 is moved across the field. However, in an alternative embodiment, the controller 114 may be configured to receive the acoustic data 122 at a predetermined sampling rate or time interval as the seed-planting implement 14 is moved across the field.

The controller 114 may be configured to monitor a soil condition(s) associated with the soil within the field based on the received acoustic data 122. More specifically, as indicated above, the furrow forming tool(s), such as the disc opener(s) 30, may be moved through the soil in a manner that forms a furrow therein. In this regard, the sound(s) created by or otherwise associated with movement of the furrow forming tool(s) through the soil may be indicative of one or more soil conditions of the soil, such as the roughness of the soil, the presence of impediments (e.g., rocks) within the soil, and/or the variation of soil material properties (e.g., soil elasticity). As such, the controller 114 may be configured to analyze the received acoustic data 122 and monitor or otherwise determine soil condition(s) of the soil based on the characteristics of the sound(s) associated with the acoustic data 122. For example, the controller 114 may include any suitable sound processing algorithms stored within its memory 118 or may otherwise use any suitable sound processing techniques to monitor the soil condition parameter(s) based on the received acoustic data 122.

As indicated, the controller 114 may be configured to monitor soil condition(s) based on the characteristics of the sound(s) associated with the acoustic data 122. More specifically, in several embodiments, the controller 114 may be configured to determine the frequency or intensity of the sound(s) associated with the acoustic data 122. Thereafter, the controller 114 may be configured to identify soil condition(s) based on the associated frequency or sound. For example, the frequency or intensity of the sound(s) may be associated with rocks or scraping. In such instances, the controller 114 may determine that there are rocks present within the soil. Moreover, in such embodiments, the controller 114 may be configured to group together sounds having similar characteristics (e.g., frequency, intensity, and/or the like). Furthermore, in one embodiment, the controller 114 may use additional data, such as data associated with the tool type, the season, the time of year, an environmental condition, and/or the like, to improve the accuracy of the sound analysis. For example, data indicative of recent precipitation may help improve such accuracy. Additionally, the controller 114 may be configured to monitor soil condition(s) based on the absence of particular sound(s) within the acoustic data 122, such as what happens when an opener is plugged and the seed is not hitting the flow guides. The controller 114 may also be configured to use previously captured and analyzed acoustic data to analyze the currently received data. As such, the controller 114 may "learn" from the previously captured acoustic data. For example, the controller 114 may use any suitable machine learning algorithm (e.g., one or more neural networks) to learn from the previously captured acoustic data.

In one embodiment, the controller 114 may be configured to monitor the soil condition(s) associated with the soil within the field based on both the received acoustic data 122 and acceleration data associated with movement of the furrow forming tool(s). Specifically, as shown in FIG. 4, the controller 114 may be communicatively coupled to the acceleration sensor 108 via a wired or wireless connection to allow acceleration data (e.g., indicated by dashed line 124 in FIG. 4) to be transmitted from the acceleration sensor 108 to the controller 114. As indicated above, the acceleration data 124 may be indicative of a parameter associated with movement of the furrow forming tool(s), such as the disc opener(s) 30, relative to the toolbar 26 of the seed-planting implement 14. In this regard, the controller 114 may be configured to analyze both the received acoustic data 122 and the received acceleration data 124 to monitor or otherwise determine the soil condition(s) of the soil. For example, the controller 114 may be configured to differentiate similar sounds within the acoustic data 122 based on the acceleration(s) of the furrow forming tool(s) at the time such sounds were detected. In certain instances, when the furrow forming tool(s) is moved through the soils having high soil roughness, the sound(s) generated by such movement may be similar to the sound(s) generated when the furrow forming tool(s) contacts rocks or other soil impediments. In such instances, the controller 114 may be configured to differentiate between such sounds based on the associated accelerations. For instance, a higher acceleration may occur when the furrow forming tool(s) contacts a rock than when the furrow forming tool(s) is moved through rough soil. As such, the controller 114 may include any suitable algorithms stored within its memory 118 or may otherwise use any suitable processing techniques to monitor the soil condition parameter(s) based on the received acoustic data 122 and the received acceleration data 124.

Furthermore, in several embodiments, the controller 114 may be configured to create a field map that identifies the monitored soil condition(s) at locations within the field. More specifically, the field map may provide an indication of the value(s) associated with the soil condition(s) at various the geographical or physical location(s) within the field. In this regard, the controller 114 may be communicatively coupled to the location sensor 112 via a wired or wireless connection to allow location data (e.g., indicated by dashed line 126 in FIG. 4) to be transmitted from the location sensor 112 to the controller 114. Based on the received location data 126, the controller 114 may be configured to monitor the geographical position of the seed-planting implement 14 and, more specifically, the row unit 28 within the field. As such, the controller 114 may be configured to associate the current value(s) associated with the soil condition(s) as determined based on the received acoustic data 122 with the current location or position of the seed-planting implement 14 within the field. For example, when it is determined that the furrow forming tool(s) has encountered a rock within the field, the controller 114 may be configured to associate the current location of the seed-planting implement 14 with the presence of a soil impediment. In one embodiment, the field map may visually identify the monitored soil condition(s) at locations within the field, such as through the use of various colors. In such embodiment, the controller 114 may be configured to display the field map to the operator of the seed-planting implement 14. e.g., via the user interface 120. However, it should be appreciated that, in alternative embodiments, the field map may have any other suitable configuration that correlates the values of the soil condition(s) to locations within the field, such as a data table or matrix.

Additionally, in one embodiment, the controller 114 may be further configured to create a field map that identifies locations of the agricultural product 16 (e.g., seeds) within the field. As indicated above, in one embodiment, the acoustic data 122 may also be indicative of the sound(s) associated with delivery of the agricultural product 16 to the furrow. As such, the controller 114 may be configured to analyze the received acoustic data 122 and monitor or otherwise determine when the agricultural product 16 is deposited into the furrow based on the characteristics of the sound(s) associated with the acoustic data 122. For example, the controller 114 may include any suitable sound processing algorithms stored within its memory 118 or may otherwise use any suitable sound processing techniques to monitor the delivery of the agricultural product 16 to the furrow based on the received acoustic data 122. In this regard, when it is determined that the agricultural product 16 has been dispensed from the row unit 28, the controller 114 may be configured to associate the current location of the seed-planting implement 14 and, more specifically, the row unit 28 with the presence of the agricultural product 16. In instances in which the agricultural product 16 corresponds to seeds, the field map may provide the locations of crops within the field, such as for use in later agricultural operations (e.g., spraying, harvesting, etc.). It should be appreciated that the controller 114 may be configured to create a single field map identifying the locations of both the soil condition(s) and the agricultural product 16 or several maps, with each map identifying the locations of one of the soil condition(s) or the agricultural product 16.

In accordance with aspects of the present subject matter, the controller 114 may further be configured to initiate a control action associated with adjusting one or more operating parameters of the seed-planting implement 14 when it is determined that the monitored soil condition(s) has fallen outside a predetermined soil condition range(s). Specifically, in several embodiments, the controller 114 may be configured to compare the values associated with the monitored soil condition to a predetermined soil condition range. Thereafter, in the event that the values of the estimated soil condition exceeds a maximum soil condition value threshold for the given soil condition value range or falls below a minimum soil condition value threshold for such range (thereby indicating that the value of the soil condition of the soil within the field may be too high or too low), the controller 114 may be configured to initiate a control action associated with adjusting an operating parameter of the seed-planting implement 14.

In one embodiment, the controller 114 may be configured to notifyi the operator of the seed-planting implement 14 that the value of the monitored soil condition has fallen outside of the predetermined soil condition value range. Specifically, in one embodiment, the controller 114 may be communicatively coupled to the user interface 120 via a wired or wireless connection to allow feedback signals (e.g., indicated by dashed line 128 in FIG. 4) to be transmitted from the controller 114 to the user interface 120. In such embodiment, the feedback signals 128 may instruct the user interface 120 to provide a notification to the operator of the seed-planting implement 14 (e.g., by causing a visual or audible notification or indicator to be presented to the operator within the cab of the work vehicle 10) that provides an indication that the value of the monitored soil condition has fallen outside of the predetermined soil condition value range. In such instances, the operator may then choose to initiate any suitable corrective action he/she believes is necessary, such as adjusting the down pressure being applied to the furrow forming tool(s) of the seed-planting implement 14.

Moreover, in several embodiments, the controller 114 may be configured to automatically adjust one or more operating parameters of the seed-planting implement 14 when it is determined that the value of the monitored soil condition has fallen outside the predetermined soil condition value range. Specifically, as shown in FIG. 4, the controller 114 may be communicatively coupled to one or more components of the seed-planting implement 14, such as actuator(s) 102, via a wired or wireless connection to allow control signals (e.g., indicated by dashed lines 130 in FIG. 4) to be transmitted from the controller 114 to the actuator(s) 102. As such, the controller 114 may be configured to transmit control signals 130 to actuator(s) 102 instructing the actuator(s) 102 to adjust the down pressure being applied to the associated disc opener(s) 30, such as by extending or retracting the corresponding rod(s) 104 relative to the corresponding cylinder(s) 106. Furthermore, in one embodiment, the controller 114 may be configured to automatically adjust one or more parameters, such as the rates at which agricultural products (e.g., seed, fertilizer, etc.) are deposited into the furrow.

Figure 5:
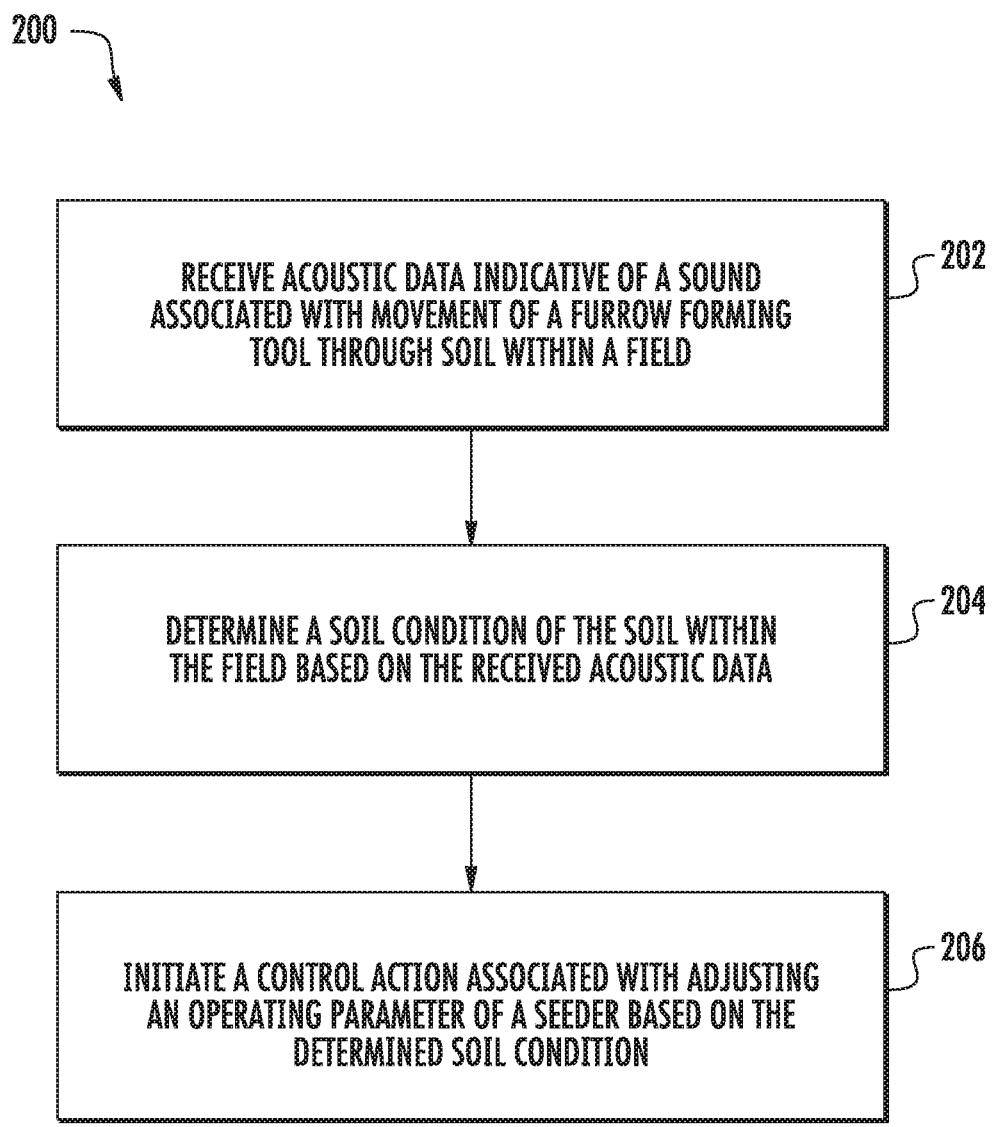
FIG. 5 illustrates a flow diagram of one embodiment of a method for controlling operating parameters of a seed-planting implement based on monitored soil conditions in accordance with aspects of the present subject matter.

Referring now to FIG. 5, a flow diagram of one embodiment of a method 200 for controlling operating parameters of a seed-planting implement based on monitored soil conditions is illustrated in accordance with aspects of the present subject matter. In general, the method 200 will be described herein with reference to the seed-planting implement 14 and the system 100 described above with reference to FIGS. 1-4. However, it should be appreciated by those of ordinary skill in the art that the disclosed method 200 may generally be utilized to adjust operating parameters of any seed-planting implement any suitable seed-planting implement configuration and/or in connection with any system having any suitable system configuration. In addition, although FIG. 5 depicts steps performed in a particular order for purposes of illustration and discussion, the methods discussed herein are not limited to any particular order or arrangement. One skilled in the art, using the disclosures provided herein, will appreciate that various steps of the methods disclosed herein can be omitted, rearranged, combined, and/or adapted in various ways without deviating from the scope of the present disclosure.

As shown in FIG. 5, at (202), the method 200 may include receiving, with a computing device, acoustic data indicative of a sound associated with movement of a furrow forming tool through soil within a field. For instance, as indicated above, the controller 114 may be communicatively coupled to the acoustic sensor 110, which is configured to detect a sound(s) associated with movement of a furrow forming tool(s), such as the disc opener(s) 30, through the soil as the seed-planting implement 14 is moved across the field. As such, the controller 114 may be configured to receive the acoustic data 122 from the acoustic sensor 110.

Additionally, at (204), the method 200 may include determining, with the computing device, a soil condition of the soil within the field based on the received acoustic data. For instance, as described above, the controller 114 may be configured to analyze the acoustic data 122 received from the acoustic sensor 110 to determine or otherwise monitor one or more soil conditions associated with the soil within the field, such as the soil roughness of and/or the presences of rocks or impediments within the soil.

Moreover, as shown in FIG. 5, at (206), the method 200 may include initiating, with the computing device, a control action associated with adjusting an operating parameter of a seed-planting implement based on the determined soil condition. For instance, as described above, the controller 114 may be configured to transmit control signals 130 to the actuator(s) 102 to adjust one or more operating parameters of the seed-planting implement 14, such as the down pressure being applied to the corresponding disc opener(s) 30, based on the determined soil condition(s).

It is to be understood that the steps of the method 200 are performed by the controller 114 upon loading and executing software code or instructions which are tangibly stored on a tangible computer readable medium, such as on a magnetic medium, e.g., a computer hard drive, an optical medium, e.g., an optical disc, solid-state memory, e.g., flash memory, or other storage media known in the art. Thus, any of the functionality performed by the controller 114 described herein, such as the method 20X), is implemented in software code or instructions which are tangibly stored on a tangible computer readable medium. The controller 114 loads the software code or instructions via a direct interface with the computer readable medium or via a wired and/or wireless network. Upon loading and executing such software code or instructions by the controller 114, the controller 114 may perform any of the functionality of the controller 114 described herein, including any steps of the methods 200 described herein.

The term "software code" or "code" used herein refers to any instructions or set of instructions that influence the operation of a computer or controller. They may exist in a computer-executable form, such as machine code, which is the set of instructions and data directly executed by a computer's central processing unit or by a controller, a human-understandable form, such as source code, which may be compiled in order to be executed by a computer's central processing unit or by a controller, or an intermediate form such as object code, which is produced by a compiler. As used herein, the term "software code" or "code" also includes any human-understandable computer instructions or set of instructions, e.g., a script, that may be executed on the fly with the aid of an interpreter executed by a computer's central processing unit or by a controller.

This written description uses examples to disclose the technology, including the best mode, and also to enable any person skilled in the art to practice the technology, including making and using any devices or systems and performing any incorporated methods. The patentable scope of the technology is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal language of the claims.

What is claimed is:

1. A system for monitoring soil conditions, the system comprising:
   a furrow forming tool;
   an acoustic sensor configured to detect a sound created by movement of the furrow forming tool through the soil; and
   a controller communicatively coupled to the acoustic sensor, the controller configured to:

determine a frequency or an intensity of the sound created by the movement of the furrow forming tool through the soil based on acoustic data received from the acoustic sensor; and monitor a soil condition associated with soil within the field based on the determined frequency or intensity.

2. The system of claim 1, wherein the furrow forming tool forms part of a seed-planting implement, the acoustic sensor is installed on the seed-planting implement at a position adjacent to the furrow forming tool.

3. The system of claim 1, further comprising:

an acceleration sensor configured to detect a parameter associated with movement of the furrow forming tool relative to a frame supporting the furrow forming tool, the controller further configured to monitor the soil condition based on both the determined frequency or intensity and acceleration data received from the acceleration sensor.

4. The system of claim 1, wherein the soil condition comprises at least one of soil roughness, a presence of soil impediments within the field, or a variation of soil material properties.

5. The system of claim 1, wherein the controller is further configured to create a field map that identifies the monitored soil condition at locations within the field based on the received acoustic data.

6. The system of claim 1, wherein the acoustic sensor is further configured to detect a sound associated with delivery of an agricultural product to a furrow formed by the furrow forming tool, the controller further configured create a field map that identifies locations of the agricultural product within the field based on the acoustic data received from the acoustic sensor.

7. The system of claim 1, wherein the acoustic sensor comprises a microphone.

8. The system of claim 1, wherein the furrow forming tool forms part of a seed-planting implement, the controller further configured to initiate a control action associated with adjusting an operating parameter of the seed-planting implement when it is determined that the soil condition has fallen outside of a predetermined soil condition range.

9. The system of claim 8, wherein the control action is associated with notifying an operator of the seed-planting implement that the soil condition has fallen outside of the predetermined soil condition range.

10. The system of claim 8, wherein the control action is associated with at least one of adjusting a down pressure applied on the furrow forming tool or adjusting a rate at which an agricultural product is dispensed by the seed-planting implement.

11. A seed-planting implement, comprising:

a frame;

a furrow forming tool mounted on the frame and configured to form a furrow within the soil;

an acoustic sensor configured to detect a sound created by movement of the furrow forming tool through the soil;

an acceleration sensor configured to detect a parameter associated with movement of the furrow forming tool relative to the frame; and a controller communicatively coupled to the acoustic sensor and the acceleration sensor, the controller configured to:

determine a frequency or an intensity of the sound created by the movement of the furrow forming tool through the soil based on acoustic data received from the acoustic sensor; and monitor a soil condition associated with soil within the field based on the determined frequency or intensity and data received from the acceleration sensor.

12. A method for controlling operating parameters of a seed-planting implement based on monitored soil conditions, the seed-planting implement including a furrow forming tool, the method comprising:

receiving, with a computing device, acoustic data indicative of a sound created by movement of the furrow forming tool through soil within a field;

determining, with the computing device, a frequency or an intensity of the sound created by the movement of the furrow forming tool through the soil based on the received acoustic data;

determining, with the computing device, a soil condition of the soil within the field based on the determined frequency or intensity; and initiating, with the computing device, a control action associated with adjusting an operating parameter of the seed-planting implement based on the determined soil condition.

13. The method of claim 12, wherein the acoustic sensor is installed on the seed-planting implement at a position adjacent to the furrow forming tool.

14. The method of claim 12, further comprising:

receiving, with the computing device, acceleration data associated with movement of the furrow forming tool relative to a frame of the seed-planting implement, wherein determining the soil condition further comprises determining, with the computing device, the soil condition of the soil within the field based on both the determined frequency or intensity and the received acceleration data.

15. The method of claim 12, wherein the soil condition comprises at least one of soil roughness or a presence of soil impediments within the field.

16. The method of claim 12, further comprising:

creating, with the computing device, a field map that identifies the soil condition at location within the field based on the received acoustic data.

17. The method of claim 12, wherein the acoustic data received from the acoustic sensor is further indicative of a sound associated with delivery of agricultural product to a furrow formed by the furrow forming tool, the method further comprising:

creating, with the computing device, a field map that identifies locations of the agricultural product within the field based on the received acoustic data.

18. The method of claim 12, further comprising:

when the soil condition has fallen outside of a predetermined soil condition range, initiating, with the computing device, the control action.

19. The method of claim 18, wherein the control action is associated with notifying an operator of the seed-planting implement that the soil condition has fallen outside of the predetermined soil condition range.

20. The method of claim 18, wherein the control action is associated with at least one of adjusting a down pressure applied to the furrow forming tool or adjusting a rate at which an agricultural product is dispensed by the seed-planting implement.

* * * * *